(12) United States Patent  
Asgeirsson et al.

(10) Patent No.: US 8,177,855 B2
(45) Date of Patent: May 15, 2012

(54) PROSTHETIC FOOT

(75) Inventors: Sigurdur Asgeirsson, Gardabaer (IS); Gudlaugur Olafsson, Vestmannaeyjar (IS); Gudni Ingimarsson, Reykjavik (IS)

(73) Assignee: Ossur hf, Reykjavik (IS)

( * ) Notice: Subject to any disclaimer, the term of this patent is extended or adjusted under 35 U.S.C. 154(b) by 0 days.

(21) Appl. No.: 12/243,748

(22) Filed: Oct. 1, 2008

(65) Prior Publication Data

US 2009/0030531 A1  Jan. 29, 2009

Related U.S. Application Data

(62) Division of application No. 11/819,844, filed on Jun. 29, 2007, now Pat. No. 7,503,937.

(60) Provisional application No. 60/861,716, filed on Nov. 30, 2006, provisional application No. 60/817,700, filed on Jul. 3, 2006.

(51) Int. Cl.
*A61F 2/66* (2006.01)
(52) U.S. Cl. .......................................................... 623/55
(58) Field of Classification Search ............... 623/47–55
See application file for complete search history.

(56) References Cited

U.S. PATENT DOCUMENTS

| | | | |
|---|---|---|---|
| 2,556,525 A | 6/1951 | Drennon | |
| 3,098,239 A | 7/1963 | Nader | |
| 3,766,569 A | 10/1973 | Orange | |
| 3,890,650 A | 6/1975 | Prahl | |
| 4,652,266 A | 3/1987 | Truesdell | |
| 4,865,612 A | 9/1989 | Arbogast et al. | |
| 5,007,938 A | 4/1991 | Prahl | |
| 5,066,305 A | 11/1991 | Firth | |
| 5,112,356 A | 5/1992 | Harris et al. | |
| 5,116,383 A | 5/1992 | Shorter et al. | |
| 5,156,632 A | 10/1992 | Wellershaus | |
| 5,376,133 A | 12/1994 | Gramnas | |
| 5,405,410 A | 4/1995 | Arbogast et al. | |
| 5,443,522 A | 8/1995 | Hiemisch | |
| 5,728,171 A * | 3/1998 | Bryant et al. ................... 623/38 |
| 5,728,177 A | 3/1998 | Phillips | |
| 5,888,239 A | 3/1999 | Wellershaus et al. | |
| 6,029,374 A | 2/2000 | Herr et al. | |
| 6,261,324 B1 | 7/2001 | Merlette | |

(Continued)

FOREIGN PATENT DOCUMENTS

EP  487 852 A1  6/1992

(Continued)

OTHER PUBLICATIONS

Supplementary European Search Report issued in related European application No. 07 810 140.9, Apr. 23, 2010.

*Primary Examiner* — Bruce E Snow
(74) *Attorney, Agent, or Firm* — Bacon & Thomas, PLLC

(57) ABSTRACT

Embodiments of low cost prosthetic feet include a footplate with a connection mechanism embedded within a first foam element having a first stiffness. A second foam element is bonded to the footplate and has a recess in a proximal surface and a stiffness greater than the first foam element. The second foam element may have a portion extending past the terminal end of the footplate. A cosmesis encloses the components of the prosthetic foot. A third foam element that extends through the cosmesis into the second foam element may be provided. The third foam element may have a higher stiffness than the first and second foam elements.

19 Claims, 2 Drawing Sheets

U.S. PATENT DOCUMENTS

| | | |
|---|---|---|
| 6,511,514 B1 | 1/2003 | Wilson |
| 6,527,811 B1 | 3/2003 | Phillips |
| 6,572,659 B1 | 6/2003 | Ryan |
| 6,811,571 B1 | 11/2004 | Phillips |
| 2002/0013628 A1 | 1/2002 | Harris |
| 2002/0040249 A1 | 4/2002 | Phillips |
| 2002/0077706 A1 | 6/2002 | Phillips |
| 2002/0128727 A1 | 9/2002 | Merlette et al. |
| 2003/0191541 A1 | 10/2003 | Phillips |
| 2005/0060045 A1 | 3/2005 | Smith et al. |
| 2005/0203640 A1 | 9/2005 | Christensen |
| 2005/0234563 A1 | 10/2005 | Phillips |
| 2005/0261783 A1 | 11/2005 | Geilman et al. |
| 2005/0267602 A1 | 12/2005 | Clausen et al. |
| 2005/0267603 A1 | 12/2005 | Lecomte et al. |
| 2006/0015192 A1 | 1/2006 | Clausen et al. |

FOREIGN PATENT DOCUMENTS

WO 2005/117749 A2 12/2005

* cited by examiner

PROSTHETIC FOOT

This application is a divisional application of U.S. patent application Ser. No. 11/819,844, filed Jun. 29, 2007, which issued on Mar. 17, 2009 as U.S. Pat. No. 7,503,937 and claims the benefit of the filing dates of U.S. Provisional Application No. 60/861,716, filed Nov. 30, 2006, and U.S. Provisional Application No. 60/817,700, filed Jul. 3, 2006.

FIELD OF THE INVENTION

The present invention relates generally to the field of prosthetic devices, and more particularly to prosthetic feet and footplates for use in therein.

BACKGROUND

In the field of prosthetics, many significant advances in construction and design of prosthetic limbs have been made possible due to improved materials and manufacturing capability. In particular, prosthetic feet and footplates for use therein have undergone large improvements in both design and construction.

The use of lightweight plastics and composite materials in prosthetic feet and footplates represents a significant improvement over the previous designs, which typically included solid blocks of wood that were cosmetically shaped. In addition, the study of biomechanics and the gait cycle have allowed for improved designs that more closely simulate the mechanics and responses of the human foot.

While the current designs of prosthetic feet and footplates represent an advance over the previous designs, a majority of the current designs have become quite complex. Due to the complexity of the designs, and material and manufacturing costs, current prosthetic feet are relatively expensive.

Due to the relatively high cost of many current prosthetic feet, people in developing and underdeveloped countries and regions of the world have limited or no access to prosthetic feet and footplates. This is especially unfortunate, as many underdeveloped and developing regions are recovering from years of civil wars and regional conflicts where the use of landmines has been rampant. Since landmines have a tendency to cause injuries to the lower extremities, there is a large need for prosthetic feet and footplates in regions that are affected by this danger. However, most of the people in developing and underdeveloped regions who are in need of prosthetic limbs are precluded access to most of the current designs because of their economic situation.

Additionally, users of prosthetic feet all over the world may not need all of the additional performance characteristics provided by complex and expensive prosthetic feet. Many users of prosthetic feet simply require a prosthetic foot that provides comfort and stability, as opposed to a prosthetic foot that must closely simulate all of the mechanics of a human foot. For example, low activity users do not require a prosthetic foot that will allow them to run and jog. An example of a low activity user may be an elderly user who may not need a complex prosthetic foot that closely simulates the behavior of the human foot, but instead may only require a prosthetic foot that provides some simulation of the human foot while providing sufficient comfort and stability.

Thus, it would be advantageous to provide functional and light-weight prosthetic feet that may be manufactured economically while providing all of the basic necessary attributes required of a prosthetic foot. Such prosthetic feet would be more accessible to more people of the world than most current designs.

SUMMARY

In order to provide low cost and improved prosthetic feet, exemplary embodiments of a prosthetic foot are described.

One embodiment of a prosthetic foot includes a resilient footplate embedded within a first foam element that has a specific density. The footplate is defined by proximal and distal surfaces, as well as anterior and posterior portions, with a terminal end located in the posterior portion. A second foam element is bonded to the distal surface of the posterior portion of the footplate and is also embedded within the first foam element. The second foam element has a density that is higher than the density of the first foam element. The second foam element also has a recess in the proximal surface of the element. Due to the recess in the second foam element, an accommodation space is formed between the proximal surface of the second foam element and the distal surface of the footplate.

In another embodiment, the prosthetic foot may have a tough outer shell that is scuff, puncture and tear resistant, and which defines a cosmesis that encloses the first and second foam elements.

In yet another embodiment, the prosthetic foot may incorporate a pyramid that is retained by a pyramid adapter, wherein at least one attachment bolt secures the pyramid and the pyramid adapter to the resilient footplate. In this embodiment, each attachment bolt includes a bolt head configured to engage the distal surface of the footplate, such that each bolt head is accommodated within the space defined between the second foam element and the footplate. At least a portion of the pyramid adapter may be embedded within the first foam element. Of course, any suitable mechanism for connecting the prosthetic foot to a prosthetic limb, socket, or pylon may be utilized in place of the pyramid connecter described.

In a variation, a posterior clearance space is located between the proximal surface of the second foam element and the distal surface of the footplate, such that the first foam element fills in the recess and encases each bolt head.

In another variation, the second foam element may have an extending portion that extends posterior to the terminal end of the resilient footplate.

In another embodiment, the prosthetic foot includes a resilient footplate embedded within a first foam element having a first density. The prosthetic foot also includes a resilient footplate embedded within a second foam element having a second density that may be the same density as the first foam element. The second density may also be greater than the first density. Again, the footplate may be defined by proximal and distal surfaces, as well as anterior and posterior portions.

The first foam element may be disposed along the proximal surface of the footplate and the second foam element may be provided along the distal surface of the footplate. A tough outer shell that is scuff, puncture and tear resistant defines a cosmesis that encloses the first and second foam elements. A third foam element having a third density may be provided such that it extends through a distal posterior surface of the cosmesis and into a distal posterior portion of the second foam element. The third density of the third foam element may be greater than the densities of the first foam element and the second foam element. The third foam element has proximal and distal surfaces and may be trapezoidal in shape, where the distal surface is larger than the proximal surface.

Again, a pyramid adapter or other suitable adapter structure may be provided, and the second foam element may have a recess in the proximal surface thereof such that a space for accommodating the connection components is formed between the second foam element and the footplate.

In alternative constructions of footplates used in the embodiments discussed above, a combination of materials may be used, such as layers of polymers and carbon fiber composites.

The numerous advantages, features and functions of the various prosthetic feet will become readily apparent and better understood in view of the following description, appended claims, and accompanying drawings. The following description is not intended to limit the scope of the prosthetic feet, but instead merely provides exemplary embodiments for ease of understanding.

BRIEF DESCRIPTION OF THE DRAWINGS

In the various figures, similar elements are provided with similar reference numbers. It should be noted that the drawing figures are not necessarily drawn to scale, but instead are drawn to provide a better understanding of the components thereof.

DETAILED DESCRIPTION OF VARIOUS EMBODIMENTS

Figure 1:
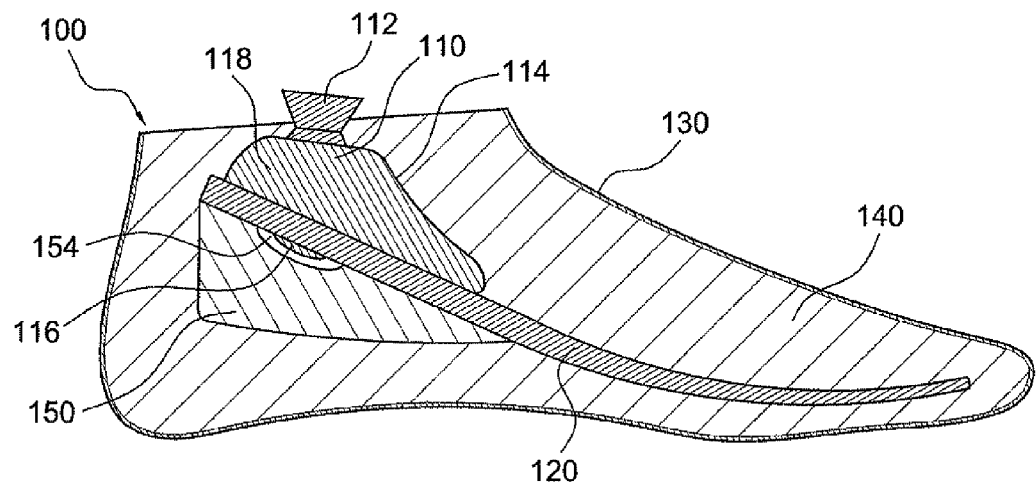
FIG. 1 is a cross-sectional view of an embodiment of a prosthetic foot.

A. Environment and Context of the Various Embodiments

The prosthetic feet in accordance with this disclosure are designed for implementation in connection with typical artificial limb hardware including prosthetic sockets, prosthetic knees, pylons and the like.

The prosthetic feet are mountable to a distal end of a pylon using a typical pyramid connection used for such applications with an adapter allowing adjustment of foot-to-pylon angles in accordance with typical adjustment features found on prosthetic feet currently offered for sale. Alternatively, clamping or threaded connections, or any other suitable connections may be used in place of the pyramid connection. Exemplary connection mechanisms are disclosed in, for example, U.S. Pat. No. 6,811,571, granted Nov. 2, 2004, and U.S. publication no. 2005/0234563, published Oct. 20, 2005, and incorporated herein by reference.

Features of the prosthetic feet include a central load bearing resilient footplate to which a connection mechanism, such as a pyramid and pyramid adapter, is secured by an attachment bolt or bolts. The footplate typically is embedded in a composite foam matrix comprising dual density, or generally a plurality of density foam elements, that provide an interface between the footplate and the surface on which a patient is supported.

1. Gait Cycle

In order to better understand the operation and benefits of the prosthetic feet described herein, a basic discussion of the gait cycle is required. The gait cycle defines the movement of the leg between successive heel contacts of the same foot. The gait cycle has two phases: stance and swing. Of particular interest in the field of prosthetic feet is the stance phase, which includes five time periods: heel-strike or initial contact, loading response, mid-stance, terminal stance, and pre-swing or toe-off.

It is during the stance phase that the mechanics of a prosthetic foot come into play. Any suitable prosthetic foot must be able to provide some cushioning during heel-strike, and some energy storage at least during mid-stance, terminal stance, and toe-off. In addition, a prosthetic foot must provide stability during mid-stance and terminal stance, at which time the entire weight of a user is transmitted through the prosthetic foot to a supporting surface.

Conventional prosthetic feet perform all of these functions, but with the tradeoff of expensive and complex designs. The embodiments of the prosthetic feet of this disclosure provide all of the basic attributes required of a prosthetic foot in an economical, lightweight design that may be economically manufactured.

2. Definitions

For further ease of understanding the prosthetic feet as disclosed herein, a description of a few terms is necessary. As used herein, the term "proximal" has its ordinary meaning and refers to a location that is closer to the heart than another location. Likewise, the term "distal" has its ordinary meaning and refers to a location that is further from the heart than another location. The ten "posterior" also has its ordinary meaning and refers to a location that is behind or to the rear of another location. Lastly, the term "anterior" has its ordinary meaning and refers to a location that is ahead of or to the front of another location.

B. Detailed Description of a First Embodiment

A first embodiment of a prosthetic foot 100 is shown in FIG. 1. The prosthetic foot 100 is constructed around a resilient footplate 120. The footplate 120 is appropriately shaped and configured to provide load bearing support and prosthetic foot characteristics permitting smooth ambulation.

Thus, the footplate 120 may be substantially planar, or may include one or more slight or gradual curves. The footplate 120 may include at least one recessed portion or cut out (not shown) in the anterior portion of the footplate 120 in order to provide what is known in the art as a "sandal toe," which allows a user to wear conventional toe strap sandals on the prosthetic foot, in addition to traditional footwear that covers the entire foot.

In an exemplary configuration, the footplate 120 may be inclined at an angle of twenty degrees with respect to the supporting surface or ground. Of course, any suitable orientation that provides the desired responsive characteristics may be utilized.

The footplate 120 is resilient so that some flexure may occur, but upon removal of loading, the footplate 120 returns to an unloaded and unflexed state. In order to accomplish this, the footplate 120 may be manufactured from carbon, carbon fiber composites, plastics, fiber reinforced plastics, molded chopped fibers, laminates, or any other suitable material.

Exemplary materials and constructions for the footplate 120 are described in U.S. Pat. No. 6,280,479, granted Aug. 28, 2001, U.S. Pat. No. 5,993,488, granted Nov. 30, 1999, and U.S. Pat. No. 5,800,569, granted Sep. 1, 1998, all of which are herein incorporated by reference.

In addition, a footplate 120 may be provided having a variety of the aforementioned materials in combination. For example, the footplate 120 may include layers of polymers and carbon fiber composites.

An exemplary attachment mechanism 110 is provided on a proximal surface of the footplate 120 and comprises a pyramid connection 112 and a pyramid adapter 114. The pyramid connection 112 is configured to be connected to a prosthetic limb support structure such as a pylon (not shown). The pyramid connection 112 and the pyramid adapter 114 may be of the conventional pyramid connections known in the art. Alternatively, the connection mechanism 110 may be of the tube and clamp type, may be a threaded connection, or comprise any other known attachment mechanisms.

Exemplary commercial embodiments of some connection types are available as part numbers A-135100, A-235300, A-335100, and A-435120 all available from Össur hf., Reykjavik, Iceland.

The connection mechanism 110 may include an intermediate portion 118 for engaging the proximal surface of the footplate 120, and receiving at least one attachment bolt 116 for adjustably and firmly retaining the connection mechanism 110 in engagement with the footplate 120. The intermediate portion 118 may have suitable coefficient of friction characteristics so that the pyramid adapter 114 will frictionally engage the footplate 120 in a manner so that the connection mechanism 110 has little to no rotational movement with respect to the footplate 120. The proximal surface of the footplate 120 may also be provided with a suitable coefficient of friction so as to prevent slippage between the footplate 120 and the connection mechanism 110. Of course, the use of multiple attachment bolts 116 further limits the relative movement between the footplate 120 and the connection mechanism 110, but adds weight to the prosthetic foot.

Preferably, a first foam element 140 surrounds and embeds the footplate 120. The first foam element 140 may have a density such that the first foam element 140 stably collapses under normal loading conditions, and thus defines a stiffness for the first foam element 140. In an exemplary embodiment the stiffness, as defined by the hardness of the first foam element 140, may be in the range of 45-55 on the Shore A scale. The foam matrix may be injection molded directly around the footplate 120, or may be molded separately and bonded to the footplate 120. The foam matrix may be any suitable open or closed cell polymer foam, such as open cell polyurethane foam.

A second foam element 150 is further embedded within the first foam element 140. The second foam element 150 may be bonded to the distal surface of the footplate 120 prior to being embedded within the first foam element 140. The second foam element 150 includes a proximal surface that has the same width as the footplate 120 in order to provide stability and may be adhesively bonded to the distal surface of the footplate 120 in a known manner. Any suitable adhesive or bonding technique may be used.

As can be seen from FIG. 1, the second foam element 150 is only bonded to a posterior portion of the footplate 120, and not across the entire distal surface of the footplate 120. In alternative embodiments, the second foam element 150 may be bonded across the entire proximal surface of the second foam element 150, or across only a portion of the proximal surface thereof.

The second foam element 150 has a higher density than the density of the first foam element 140, and thus has a higher stiffness. In other words, the second foam element 150 will stably collapse under a higher loading than the first foam element 140. For example, the second foam element 150 may have a stiffness, as defined by the hardness of the second foam element 150 of about 60 on the Shore A scale. Of course, any suitable second foam element 150 having a higher stiffness than the first foam element 140 may be used.

The second foam element may be any suitable open or closed cell polymer foam, such as open cell polyurethane foam, and may be made from the same or different foam from the first foam element 140.

The second foam element 150 includes a recessed portion 154 in the proximal surface thereof. The recess 154 may span the entire proximal surface from both sides of the second foam element 150, or may be wholly contained between the sides of the second foam element 150. When the second foam element 150 is placed in contact with the distal surface of the footplate 120, the recessed portion forms an accommodation space between the footplate 120 and the second foam element 150.

The accommodation space is configured to accommodate the head of each attachment bolt 116. Thus, bonding the second foam element 150 to the distal surface of the footplate 120 is made easier, since the proximal surface of the second foam element 150 will correspondingly mate flushly with the distal surface of the footplate 120 in both the posterior and anterior portions. Therefore, the attachment bolt head does not cause an imbalance mating between the second foam element 150 and the footplate 120. In an alternative configuration, a discrete recess may be provided for each attachment bolt head.

As can be seen in FIG. 1, the second foam element 150, as well as the footplate 120, and at least a portion of the pyramid connector 114 are all embedded within the foam matrix that defines the first foam element 140. A tough outer shell 130 that is scuff, puncture, and tear resistant may be provided around and encasing the first foam element 140 in order to provide a cosmetically pleasing appearance for the prosthetic foot 100. Such coverings are typically called a "cosmesis," and may be dyed or manufactured in different colors to represent different skin tones, as is known in the alt.

The cosmesis shell 130 may be a separate outer covering that encases the first foam element 140, and thus the remaining components of the prosthetic foot 100. Alternatively, the outer surface of the first foam element 140 may itself be treated, for example under applied heat, in order to form the cosmesis shell 130 integrally with the first foam element 140. In the instance where the cosmesis shell 130 is formed integral with the first foam element, the stiffness of the cosmesis shell 130 may be in the range of 45-55 on the Shore A scale.

According to one embodiment, the second foam element 150 may have a suitable higher density than the density of the first foam element 140 due to the fact that it must absorb heel-strike stresses and provide appropriate spring-action and cushioning that cooperates with the characteristics of the resilient footplate 120 within the prosthetic foot 100. The resilient footplate 120 provides the major support and toe-off spring action required for a prosthetic foot while the combination of the first foam element 140 and the second foam element 150 provide the heel-strike characteristics desired of a prosthetic foot. It will be noted that the resilient footplate 120 in this embodiment provides limited heel energy absorption or energy return and it is intended that the second foam element 150 in combination with the surrounding first foam element 140 will provide such desired heel-strike shock absorption and energy return functions.

Providing a prosthetic foot 100 according to this construction yields numerous advantages. One advantage is that the stiffer second foam element 150 located in the heel portion of the prosthetic foot 100 provides improved heel-strike cushioning, but reduces the energy return within the heel. This of course leads to an economical construction that maintains stability without sacrificing cushioning during the heel-strike.

Another advantage is in the ease and lowered costs of manufacturing the prosthetic foot 100. For example, this design provides the ability to manufacture a prosthetic foot and cosmesis at relatively low cost using rapid molding procedures, without the need for machining structural materials or otherwise using costly casting molds and high temperature settable materials.

One method of making the prosthetic foot 100 involves assembling the pyramid 112, pyramid adapter 114 and attachment bolts 116 together with the footplate 120 as a first assembly, then gluing the second foam element 150 to the posterior portion of the footplate 120, molding this entire assembly within a first foam element 140, and curing the first foam element 140 into a set and stable condition required of a foot cosmesis 130. Of course, other molding and assembly steps could be used to achieve the same end, as would be known to one of ordinary skill in the art.

It should be noted that if the preceding process is used and the recess 154 extends across the entire proximal surface of the second foam element 150, or if the second foam element 150 is not bonded to the footplate 120 across the entire proximal surface of the second foam element 150, the foam matrix defining the first foam element 140 may fill in the excess space within the recess 154.

Prosthetic feet according to the present invention can be made rapidly and at relatively low cost. Such prosthetic feet have application all over the world and in particular in underdeveloped regions of the world where low cost and speed of production are critical to providing prosthetic leg and feet devices for persons of lower income where cost and simplicity is a major factor, along with appearance.

C. Detailed Description of Second and Third Embodiments

Figure 2:
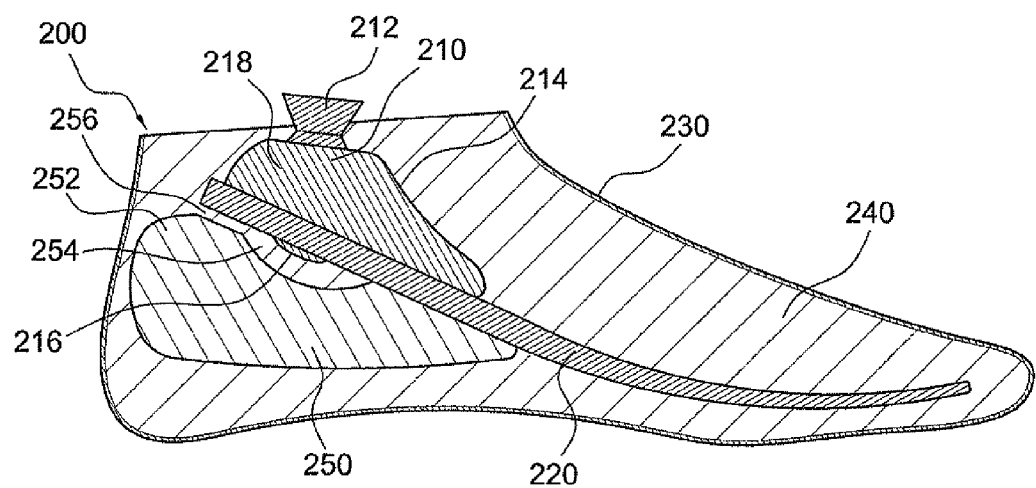
FIG. 2 is a cross-sectional view of another embodiment of a prosthetic foot.
Figure 3:
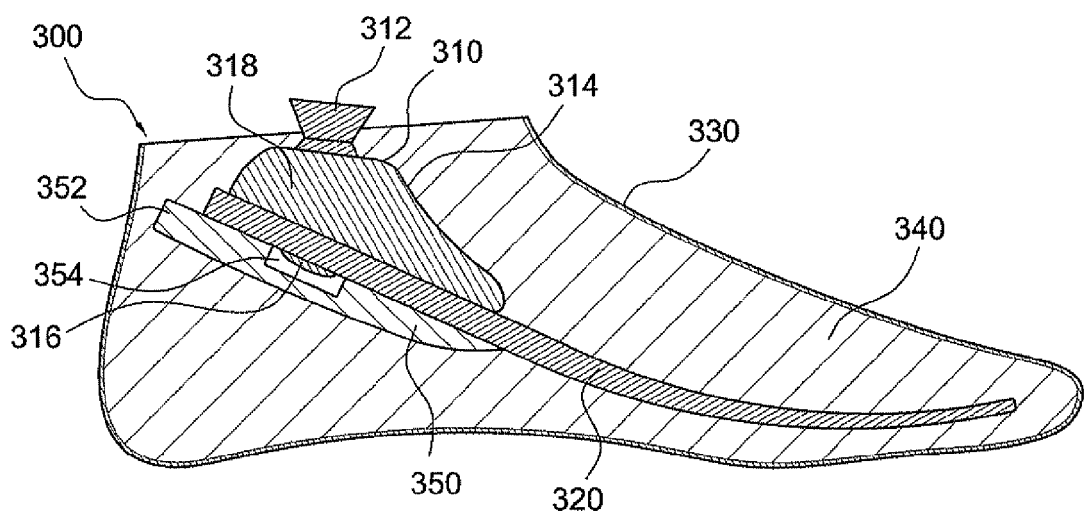
FIG. 3 is a cross-sectional view of still another embodiment of a prosthetic foot.

With reference to FIGS. 2 and 3, alternative embodiments of a prosthetic foot 200, 300, respectively include, a second foam element 250, 350 having a posterior extending portion 252, 352 that extends past a terminal end of the footplate 220, 320.

The embodiments shown in FIGS. 2 and 3 are similar to the embodiment shown in FIG. 1 and described above. A prosthetic foot 200, 300 has a footplate 220, 320, of any type previously discussed, and a connection mechanism 210, 310 for connecting the prosthetic foot 200, 300 to a prosthetic limb or pylon.

The exemplary connection mechanism 210, 310 is similar to the one previously discussed above in relation to the first embodiment. The connection mechanism includes a pyramid 212, 312, a pyramid adapter 214, 314, and at least one attachment bolt 216, 316, used to adjustably and firmly connect the intermediate portion 218, 318 of the connection mechanism 210, 310 to the footplate 220, 320. Of course, any suitable attachment mechanism may be used.

The prosthetic foot 200, 300, includes a first foam element 240, 340 and a second foam element 250, 350, and a cosmesis shell 230, 330. As before, the second foam element 250, 350 has a higher density, and hence a higher stiffness, than the first foam element 240, 340. The second foam element 250, 350 also has a recess 254, 354 that performs and functions in the same manner as previously discussed.

One difference in these embodiments is that the second foam element 250, 350 has a posterior extending portion 252, 352 that extends beyond the terminal end of the footplate 220, 320. This construction provides at least in part, the benefit of improved heel-strike cushioning and energy return.

It will be recognized that the footplate 220, 320 bears the weight of the prosthetic foot 200, 300, and provides the toe-off characteristics desired of such feet. The second foam element 250, 350 with the posterior extending portion 252, 352 provides suitable energy storage and return for heel-strike cushion and action, including energy return as the prosthetic foot 200, 300 is rotated by normal stepping action (plantar flexion and dorsiflexion).

In the variation shown in FIG. 2, a posterior clearance space 256 is shown between the proximal surface of the second foam element 250 and the footplate 220. This posterior clearance space 256 allows the first foam element 240 to fill in the recess and encase the bolt head 216 of the pyramid adapter 214. This configuration allows the second foam element 250 to be bonded to the footplate 220 prior to attaching the pyramid adapter 214 to the footplate 220.

Alternatively, as discussed above, the second foam element 250 may be more easily bonded to the footplate 220 since the bolt head 216 is accommodated in the recess, thus allowing a flush mating between the proximal surface of the second foam element 250 and the distal surface of the footplate 220. In either case, the posterior clearance space 256 allows the first foam element 240 to fill in the recess and encase the bolt head 216 in order to remove any voids in the prosthetic foot 200.

As can be seen in FIGS. 2 and 3, the second foam element 250, 350 can have varied size and shape. A skilled artisan will recognize that the size and shape of the second foam element 250, 350 can be chosen to provide the appropriate biomechanical functions of the prosthetic foot 200, 300.

For example, while walking on a supporting surface the prosthetic foot will cycle through contacting the supporting surface, partially contacting the supporting surface, not contacting the supporting surface, partially contacting the supporting surface, and back to contacting the supporting surface. One of the instances where the prosthetic foot is partially contacting the supporting surface is heel-strike. During heel-strike the posterior portion of the prosthetic foot will undergo compression as the user transfers their entire weight from one foot to the other. The first and second foam elements will all resist the compression force and therefore provide support for the user's weight. Due to the cellular structure of the first and second foam elements the elements will collapse in a stable manner as the compression force in the posterior portion increases.

The stable collapse of the first and second foam elements provides cushioning for the heel-strike, and energy storage and return for the remaining portion of the gait cycle. Since the second foam element has a higher density and stiffness than the first foam element it will not stably collapse at the same time as the first foam element but will stably collapse under an increased load. Thus, the energy storage and return provided by the second foam element is different from that provided by the first foam element.

As the user progresses through the gait cycle, the compression loading in the posterior portion of the prosthetic foot is reduced, while the rest of the prosthetic foot becomes subject to a compression loading until both the posterior and anterior portions of the prosthetic foot are in contact with the supporting surface, at mid-stance. The compression loading is more evenly distributed throughout the prosthetic foot at this point, but is slightly larger in the posterior portion due to the off-set location of the connection mechanism. Both the first and second foam elements have provided some energy return during the transition of the prosthetic foot from being in partial contact with the supporting surface to being in contact with the supporting surface.

During both heel-strike and mid-stance, the footplate may flex slightly, thus providing some additional energy storage and return. Still, a large amount of the energy storage and return are provided by the first and second foam elements. The footplate begins to flex to a greater degree during the next stage of partial contact, or heel-off. During heel-off the second foam element has returned to an almost completely uncompressed state and has returned almost all of the energy that was stored therein. The anterior portion of the footplate is now in contact with the supporting surface, so the first foam element in the anterior region may be compressed to provide additional energy storage and return along with the footplate.

When the entire prosthetic foot has been lifted from the supporting surface and is no longer in contact with the supporting surface, the elements, in particular the footplate, of the prosthetic foot have provided energy return and are unstressed. Thus the cycle repeats with another heel-strike and so on.

Thus, it is evident that altering the sizes and shapes of the components of the prosthetic foot 200, 300 can affect the biomechanical properties, such as stability, energy absorption and energy return, of the prosthetic foot 200, 300. For example, the second foam element 250 in FIG. 2 has a large portion 252 extending past the terminal end of the footplate 220. This configuration provides more stability, balanced against a decrease in energy absorption and return. The embodiment of FIG. 3 provides a balance between stability and energy absorption and return by reducing the size of the second foam element 350, and in particular the portion 352 that extends past the terminal end of the footplate 320. The reduced size of the second foam element 350 in FIG. 3, allows a greater amount of the first foam element to be located beneath the heal portion of the footplate 320. Thus, the embodiment of FIG. 3 provides increased energy absorption balanced against a slight decrease in stability.

It will be recognized that the discussion above detailing variations in materials and construction of the components of the prosthetic foot are equally applicable to these embodiments.

D. Detailed Description of a Fourth Embodiment

Figure 4:
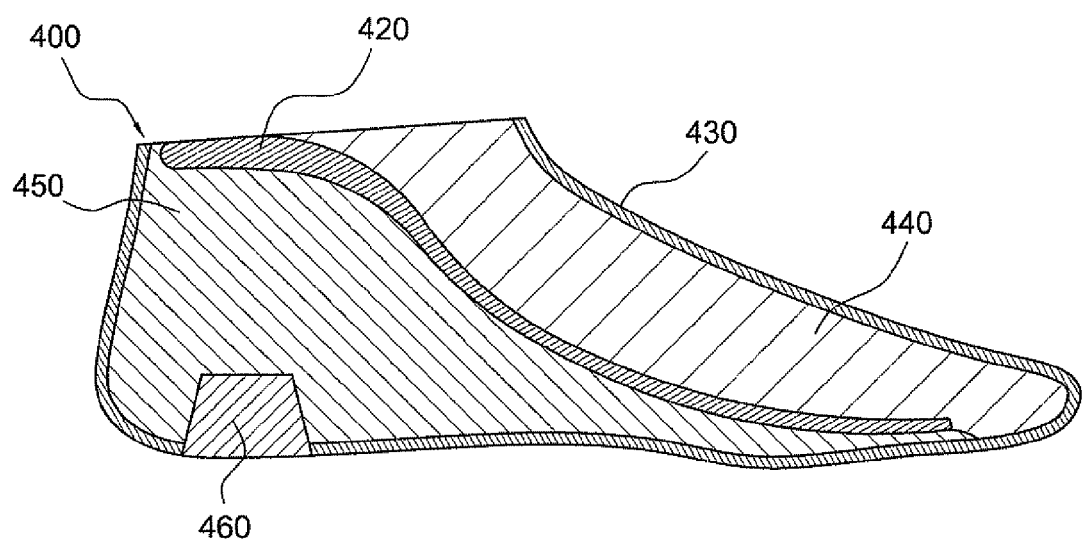
FIG. 4 is a cross-sectional view of yet another embodiment of a prosthetic foot.

A fourth embodiment of a prosthetic foot 400 is shown in FIG. 4. A footplate 420, of any type previously discussed herein, is provided embedded between a first foam element 440 and a second foam element 450. The first and second foam elements 440, 450 may be made from materials previously discussed and may have the same density and stiffness. For example, the first and second foam elements 440, 450 may be made from an ethylene vinyl acetate (EVA) closed or open cell foam having a stiffness, as measured by the hardness, in the range of 45 to 55 on the Shore A scale.

Alternatively, the second foam element 450 may have a higher density, and thus a higher stiffness than the density of the first foam element 440. Both the first and second foam elements 440, 450 may be separately molded by known techniques and bonded to the footplate 420. Of course, the first and second foam elements 440, 450 may also be simultaneously molded integrally around the footplate 420 in a known manner.

A cosmesis shell 430 of the type previously discussed is provided around and enclosing the first and second foam elements 440, 450, as well as the footplate 420. Of course, the prosthetic foot 400 may also include any of the connection mechanisms previously discussed for connecting the prosthetic foot 400 to a pylon of a prosthetic limb (not shown). The connection mechanism may be partially enclosed within the cosmesis shell 430, as discussed above. Although not shown, the second foam element 450 can include a recess for accommodating the heads of any attachment bolts used to attach the connection mechanism to the footplate 420, in the manner discussed above.

A third foam element 460 is provided that extends through a distal posterior surface of the cosmesis shell 430 and into the second foam element 450. The third foam element 460 as shown extends into a distal posterior portion of the second foam element 450. The specific location and size of the third foam element 460 with respect to the second foam element 450 may be chosen in any appropriate manner in order to provide the desired biomechanical properties of the prosthetic foot 400. For example, the width of the third foam element may be larger than the width of the footplate 420, and nearly as wide, or as wide as the width of the cosmesis shell 430 in order to cover or nearly cover the entirety of the ground or supporting surface contact area.

The third foam element 460 can have a higher density, and hence a higher stiffness than the densities and stiffnesses of both the first and second foam elements 440, 450. Again, all of the foam elements may be made from the same or different materials, including open or closed cell polymer foams such as closed cell polyurethane foams. Also, the size and shape of the third foam element 460 may be varied and chosen based upon the intended effect on the biomechanical properties of the prosthetic foot 400.

This embodiment provides another low-cost prosthetic foot that performs all of the necessary functions of a prosthetic foot and is easy to manufacture using known molding techniques. As previously discussed, a stiffer heel insert provides good stability during mid-stance and terminal stance, while still providing ample cushioning and energy return during heel-strike.

F. Conclusion

These embodiments provide great flexibility for economic prosthetic feet that provide an alternative to the complex and more expensive prosthetic feet currently in use.

It is understood that the size of the prosthetic feet and the components thereof can be adjusted so that many different users having different sized feet may benefit from the present design of prosthetic feet. Specifically, the width, thickness and length of the footplates may be varied to accommodate different sized users. Accordingly, the size of the foam elements may be respectively varied along with the different sized footplates. Further, the size of the cosmesis may also be varied to surround the different sized foam elements and footplates. Exemplary considerations of cosmesis and prosthetic foot size are disclosed in U.S. Pat. Nos. 5,800,569, 5,993,488, and 6,280,479, granted respectively on Sep. 1, 1998, Nov. 30, 1999, and Aug. 28, 2001 and herein incorporated by reference.

Of course, it is to be understood that not necessarily all objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

The skilled artisan will recognize the interchangeability of various features from different embodiments. In addition to the variations described herein, other known equivalents for each feature can be mixed and matched by one of ordinary skill in this art to construct a prosthetic foot in accordance with principles of the present invention.

Although this invention has been disclosed in the context of certain exemplary embodiments and examples, it therefore will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above, but should be determined only by a fair reading of the claims below.

The invention claimed is:

1. A prosthetic foot comprising:
a first foam element having a first stiffness and substantially defining an outer periphery of the prosthetic foot;
a resilient footplate embedded within the first foam element, and having proximal and distal surfaces, and anterior and posterior portions;
a second foam element embedded within the first foam element and bonded to the distal surface of the posterior portion of the footplate, and further defining a recess along a proximal surface thereof, the second foam element having a second stiffness greater than the first stiffness of the first foam element;
wherein the recess of the second foam element forms an accommodation space between the proximal surface of the second foam element and the distal surface of the footplate;
wherein the bonding of the second foam element to the footplate allows a flush mating between the proximal surface of the second foam element and the distal surface of the footplate; and
the first foam element fills in the accommodation space.

2. A prosthetic foot comprising:
a first foam element having a first stiffness and substantially defining an outer periphery of the prosthetic foot;
a resilient footplate embedded within the first foam element, and having proximal and distal surfaces, and anterior and posterior portions;
a second foam element embedded within the first foam element and bonded to the distal surface of the posterior portion of the footplate, and further defining a recess along a proximal surface thereof, the second foam element having a second stiffness greater than the first stiffness of the first foam element;
wherein the recess of the second foam element forms an accommodation space between the proximal surface of the second foam element and the distal surface of the footplate; and
further comprising a posterior clearance space near a posterior portion between the proximal surface of the second foam element and the distal surface of the footplate, such that the first foam element fills in the recess of the second foam element.

3. The prosthetic foot according to claim 2, further comprising:
a pyramid adapter;
a pyramid retained by the pyramid adapter; and
at least a portion of the pyramid adapter being embedded within the first foam element.

4. The prosthetic foot according to claim 3, further comprising:
at least one attachment bolt securing the resilient foot plate to the pyramid adapter and the pyramid;
each attachment bolt extending through the footplate and further having a bolt head that is configured to engage the distal surface of the footplate; and
each bolt head accommodated within the recess of the second foam element between the proximal surface of the second foam element and the distal surface of the footplate.

5. The prosthetic foot according to claim 2, wherein the second foam element further includes an extending portion that extends beyond a terminal end of the posterior portion of the footplate.

6. The prosthetic foot according to claim 2, further comprising:
a scuff, puncture and tear resistant outer shell defining a cosmesis that surrounds a substantial portion of the outer periphery wherein the stiffness of the cosmesis is within the range of 45-55 on the Shore A scale.

7. The prosthetic foot according to claim 2, and the stiffness of the first foam element is within the range of 45-55 on the Shore A scale.

8. The prosthetic foot according to claim 2, wherein the footplate is a carbon or carbon fiber composite footplate.

9. A prosthetic foot comprising:
a first foam element having a first stiffness and substantially defining an outer periphery of the prosthetic foot;
a resilient footplate embedded within the first foam element, and having proximal and distal surfaces, and anterior and posterior portions;
a second foam element embedded within the first foam element and bonded to the distal surface of the posterior portion of the footplate, and further defining a recess along a proximal surface thereof, the second foam element having a second stiffness greater than the first stiffness of the first foam element, and wherein the second foam element further includes an extending portion that extends beyond a terminal end of the posterior portion of the footplate;
a posterior clearance space near a posterior portion between the proximal surface of the second foam element and the distal surface of the footplate, such that the first foam element fills in the recess of the second foam element;
wherein the recess of the second foam element forms an accommodation space between the proximal surface of the second foam element and the distal surface of the footplate.

10. The prosthetic foot according to claim 9, further comprising:
a pyramid adapter;
a pyramid retained by the pyramid adapter; and
at least a portion of the pyramid adapter being embedded within the first foam element.

11. The prosthetic foot according to claim 10, further comprising:
at least one attachment bolt securing the resilient foot plate to the pyramid adapter and the pyramid;
each attachment bolt extending through the footplate and further having a bolt head that is configured to engage the distal surface of the footplate; and
each bolt head accommodated within the recess of the second foam element between the proximal surface of the second foam element and the distal surface of the footplate.

12. The prosthetic foot according to claim 11, further comprising a posterior clearance space located between the proximal surface of the second foam element and the distal surface of the footplate, such that the first foam element fills in the recess and encases each bolt head.

13. The prosthetic foot according to claim 9, further comprising:
a scuff, puncture and tear resistant outer shell defining a cosmesis that surrounds a substantial portion of the outer periphery.

14. The prosthetic foot according to claim 13, wherein the stiffness of the cosmesis is within the range of 45-55 on the Shore A scale.

15. The prosthetic foot according to claim 9, wherein the stiffness of the first foam element is within the range of 45-55 on the Shore A scale.

16. The prosthetic foot according to claim 9, wherein the stiffness of the second foam element is about 60 on the Shore A scale.

17. The prosthetic foot according to claim 9, wherein the footplate is a carbon or carbon fiber composite footplate.

18. The prosthetic foot according to claim 9, wherein the footplate is a plastic or fiber reinforced plastic footplate.

19. The prosthetic foot according to claim 9, wherein the footplate is a molded chopped fiber footplate.

\* \* \* \* \*